United States Patent [19]
Wise et al.

[11] Patent Number: 5,398,558
[45] Date of Patent: Mar. 21, 1995

[54] APPARATUS FOR SAMPLING MATERIAL

[75] Inventors: Jack C. Wise; Carter D. Clary; Gwynn A. Sawyer Ostrom, all of Clovis, Calif.

[73] Assignee: 100% California State University Fresno Foundation, Fresno, Calif.

[21] Appl. No.: 122,778

[22] Filed: Sep. 16, 1993

[51] Int. Cl.$^6$ .................... G01N 33/02; G01N 35/02; G01N 35/06
[52] U.S. Cl. ............... 73/863.53; 73/863.41; 73/863.56
[58] Field of Search ........... 73/863.41, 863.42, 863.44, 73/863.45, 863.51, 863.52, 863.53, 863.54, 863.55, 863.56

[56] References Cited

U.S. PATENT DOCUMENTS

| 27,852 | 3/1960 | Van Gelder . | |
|---|---|---|---|
| 291,474 | 1/1984 | Finch . | |
| 1,088,638 | 2/1914 | Urquhart . | |
| 1,223,544 | 4/1917 | Wendell | 73/863.41 |
| 3,302,769 | 2/1967 | Platzer et al. . | |
| 3,373,615 | 3/1968 | Silver et al. | 73/863.53 |
| 3,875,803 | 4/1975 | Clewlon | 73/863.53 |
| 3,943,771 | 3/1976 | Handa et al. . | |
| 4,252,018 | 2/1981 | Neises . | |
| 4,326,425 | 4/1982 | Gundersen et al. | 73/863.53 |
| 4,558,602 | 12/1985 | Redding | 73/863.53 |
| 5,103,683 | 4/1992 | Lyons . | |

FOREIGN PATENT DOCUMENTS

| 252528 | 4/1963 | Australia | 73/863.53 |
|---|---|---|---|
| 752634 | 12/1970 | Belgium | 73/863.53 |
| 187841 | 9/1985 | Japan | 73/863.41 |
| 561890 | 6/1977 | U.S.S.R. | 73/863.52 |
| 862035 | 9/1981 | U.S.S.R. | 73/863.53 |
| 1170315 | 7/1985 | U.S.S.R. | 73/863.41 |
| 1430797 | 10/1988 | U.S.S.R. | 73/863.41 |
| 1545139A | 2/1990 | U.S.S.R. . | |

*Primary Examiner*—Hezron E. Williams
*Assistant Examiner*—Daniel S. Larkin
*Attorney, Agent, or Firm*—Worrel & Worrel

[57] ABSTRACT

An apparatus for collecting material from a mass of the material, the apparatus having a housing for receiving the material; a container for holding the material; and an assembly mounting the housing for movement along a path through the mass of material, for the receipt of a portion of the material within the housing, and toward the container, for the release of the portion of the material into the container.

7 Claims, 3 Drawing Sheets

APPARATUS FOR SAMPLING MATERIAL

BACKGROUND OF THE INVENTION

1. Field of the Invention

The present invention relates to a sampling apparatus and, more particularly, to a sampling apparatus operable to collect material, such as fungible material, from a continuous stream thereof and to such a sampling apparatus having particular utility in the sampling of raisins during processing.

2. Description of the Prior Art

There are many environments in which it is necessary to extract material from a substantially continuous stream of such material. For example, in the manufacturing or processing of products, it is frequently necessary to remove products from the production line for examination so as to confirm that they are of the desired standard of quality, or that they are not below an established minimum standard of quality. If the samples do not meet preestablished criteria, remedial action can be taken. Known as "sampling," it is desirable that those products removed from the stream for examination, to the extent possible, be selected in such a manner as to be as representative of all of the products passing in the stream.

Where the material to be extracted from the stream consists of fungible food products, the standards for sampling are most stringent, either because of governmental regulation or because of internal concerns in the maintenance of predefined standards of quality. With the periodic public notoriety regarding instances of the contamination and adulteration of food products, the probability is that even more severe standards will be adopted. Independently thereof, it is certain that the manufacturers, processors and handlers of food products will seek to improve upon their own sampling, examination and testing procedures so as to maintain high standards of quality and to minimize the risk of injury to the public.

An illustrative environment relative to these concerns is the production, processing and handling of raisins. Although sampling may be performed at other points in the production, processing and handling of raisins, perhaps the most notable example is the sampling of raisins for examination by inspectors on behalf of the United States Department of Agriculture. The sampling of incoming lots of raisins for examination presents unique difficulties. The current method for collecting samples of raisins for examination is manual or, in other words, literally by hand. Typically, the collection process includes the sampling of raisins from the continuous stream of raisins released from the discharge chute of a device known as a "shaker table." The raisins are passed over the shaker table for the removal of foreign material from the raisins. The raisins collected as samples are literally removed by hand frown the stream at the discharge chute on a periodic basis. The samples are collected and representative portions thereof tested, on site, for moisture content, sugar content and the like.

It is evident that such conventional sampling methods are prone to inaccuracy since the collected samples are frequently not truly representative of the lot from which they were collected; that is, the timing and location in the stream of the collection do not ensure the collection of samples representative of the whole. In addition, this method is time consuming for the inspectors who could more productively devote their attention to other duties. With or without conscientious effort, conventional methods are, as a practical matter, entirely inadequate for the purpose. Thus, the samples collected for inspection and the resulting dependability of the overall inspection process are adversely affected by the inaccuracy of the sampling method.

Therefore, it has long been known that it would be desirable to have a sampling apparatus which is adaptable for use in sampling material, such as fungible goods transported in a substantially continuous stream; which is significantly more reliable than conventional methods and apparatuses intended for the same purpose; which is uniquely well suited to the sampling of incoming lots of raisins in such a manner as to ensure that the samples collected are representative of the lot sampled; which operates substantially automatically with little or no attention by personnel; which is entirely safe and dependable in operation, and is inexpensive to install, maintain and operate; and which is otherwise entirely successful in achieving its operational objectives.

SUMMARY OF THE INVENTION

Therefore, it is an object of the present invention to provide an improved sampling apparatus.

Another object is to provide such an apparatus which is adaptable for use in sampling virtually any type of material, but which is particularly well suited to the sampling of fungible goods from a substantially continuous stream thereof for examination and in such a manner that the samples so collected are significantly more representative of the lot from which the samples were collected than has heretofore been possible.

Another object is to provide such an apparatus which collects the samples substantially continuously and on a representative, rather than a random, basis.

Another object is to provide such an apparatus which achieves the ability to establish higher levels of quality control for such products are food intended for human consumption by collecting samples which are more representative of the lots from which they were obtained.

Another object is to provide such an apparatus which can operate reliably without the presence of personnel freeing such personnel for other duties.

Another object is to provide such an apparatus which can readily be installed and operated in virtually any environment in which it is desired that samples be collected and in a variety of embodiments individually adapted to the specific environments of use.

Another object is to provide such an apparatus which is particularly well suited to the collection of samples from incoming lots of food products such as raisins.

Another object is to provide such an apparatus which operates dependably without, in any way, interfering with the operation of equipment upon which it is mounted and with which it interoperates.

Further objects and advantages are to provide improved elements and arrangements thereof in an apparatus for the purpose described which is dependable, economical, durable and fully effective in accomplishing its intended purpose.

These and other objects and advantages are achieved, in the preferred embodiment of the present invention, in a sampling apparatus having a plurality of collection cups; means operable to pass the collection cups through the material to be sampled for individual receipt of samples of the material therewithin; a collection container for receiving said samples; and a mechanism for individually, successively releasing the samples from the collection cups into the collection container.

DESCRIPTION OF THE PREFERRED EMBODIMENT

Figure 1:
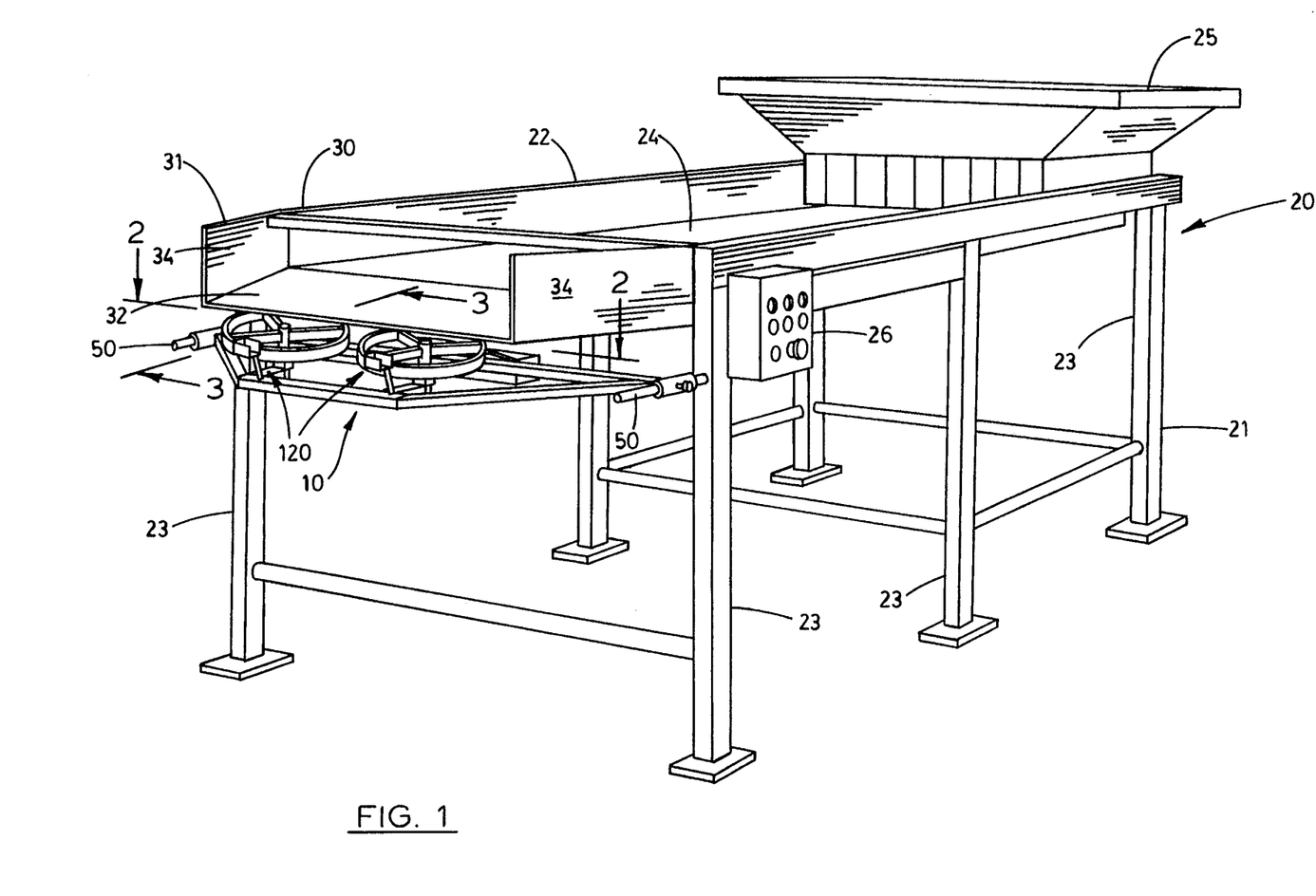
FIG. 1 is a perspective view of a conventional raisin shaker table with the sampling apparatus of the present invention mounted thereon.

Referring more particularly to the drawings, the sampling apparatus of the present invention is generally indicated by the numeral 10 in FIG. 1.

The sampling apparatus 10 is adaptable for use in a wide variety of specific environments in sampling material, as will hereinafter be described. The sampling apparatus is particularly well suited to sampling fungible goods, or, in other words, those products which are produced, or processed, in prodigious quantities and are, for all practical purposes, interchangeable. Because of its dependability in consistently collecting samples which are representative of the lots from which the samples were taken, the sampling apparatus has particular utility in sampling fungible food products, such as raisins. The sampling apparatus is described herein as employed in the sampling of raisins only as an illustrative embodiment and is not to be limited thereto.

In this illustrative environment, a raisin shaker table is generally indicated at 20 in FIG. 1. The shaker table has a main frame 21 including a table bed 22 supported on a plurality of table legs 23 mounted thereon and extending downwardly for engagement with a surface of support. The shaker table is of conventional construction, except for the sampling apparatus of the present invention which is mounted thereon, as will hereinafter be described. The shaker table has a screen assembly 24 mounted in the table bed which is reciprocable in the table bed in such a manner as to shake raisins transported along the table bed and across the screen assembly. A receiving trough, or hopper, 25 is mounted on the table bed at one end thereof and is adapted to receive raisins discharged from bins therewithin and to feed the raisins so received onto the screen assembly for such shaking in a more or less evenly distributed layer. A control housing 26 is operable, through subsystems, not shown, to operate the shaker table.

The table bed 22 of the shaker table 20 has a discharge end portion 30 opposite from the hopper 25. A discharge trough, or chute, 31 is mounted on the discharge end portion 30 of the table bed and includes a lower panel 32 sloping slightly downwardly from right to left as viewed in FIG. 3 to a lip 33. The discharge chute has convergent side walls 34 which are convergent in a direction from right to left as viewed in FIG. 3. For illustrative convenience, a multiplicity of raisins 35 are shown passing in the discharge chute 31 from right to left as viewed in FIG. 3 and discharged therefrom in a substantially continuous stream as shown therein.

As previously noted, with the exception of the sampling apparatus 10 heretofore identified, the structure heretofore described is entirely conventional. From this point forward, the sampling apparatus of the invention is described. The sampling apparatus includes a pair of cylindrical mounting rods 50 individually mounted, as by welding, on the table legs 23 on opposite sides of and beneath the discharge end portion 30 of the table bed 22. The mounting rods extend in parallel relation therefrom as shown in FIG. 2 and have cylindrical surfaces 51.

Figure 2:
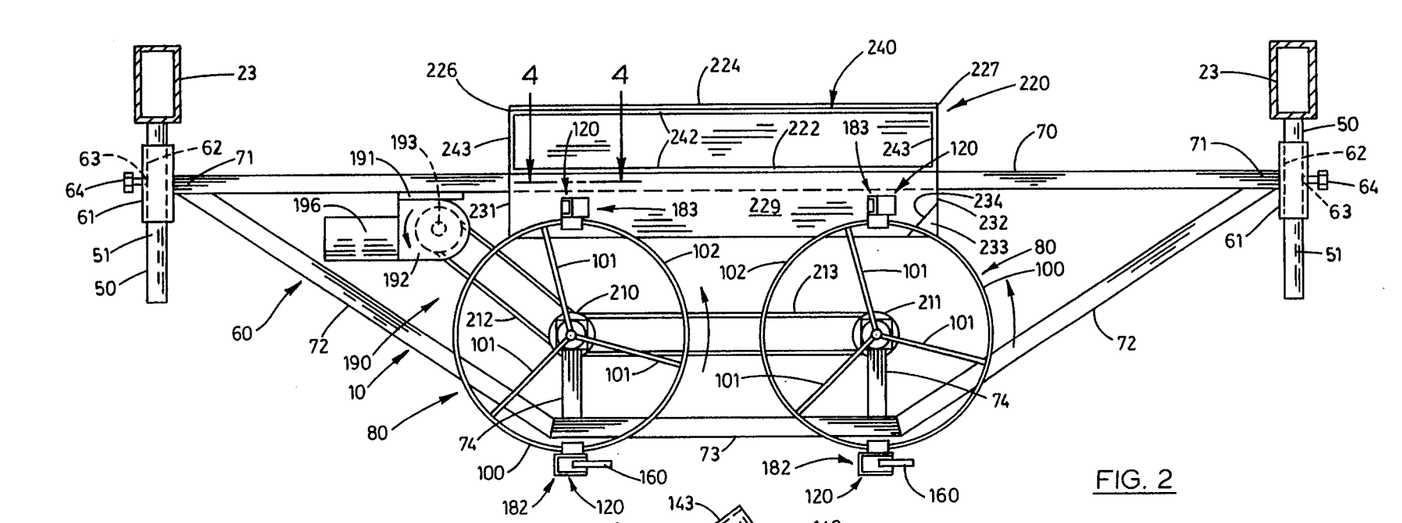
FIG. 2 is a somewhat enlarged horizontal section taken from a position indicated by line 2—2 in FIG. 1.

The sampling apparatus 10 has a main frame 60 including a pair of tubular sleeves 61 individually having internal cylindrical passages 62 of diameters permitting them individually to be slidably received on the mounting rods 50, as shown in FIG. 2. Each of the tubular sleeves has a screw threaded bore 63 extending therethrough into communication with the cylindrical passage 62 thereof. A bolt 64 is individually, screw-threadably received in the screw threaded bore of each tubular sleeve and is tightened into engagement with the cylindrical surface 51 of its respective mounting rod within the cylindrical passage thereof so as to mount the sleeves on their respective rods, as shown in FIG. 2.

The main frame 60 has a tubular cross member 70 mounted, as by welding, on and interconnecting the tubular sleeves 61 so as to extend therebetween in substantially right angular relation to the mounting rods 50. The cross member has opposite end portions 71 which are the portions of the cross member individually, weldably mounted on their respective tubular sleeves. The main frame has tubular convergent members 72 individually mounted, as by welding, on the opposite end portions 71 of the cross member 70 and extending obliquely toward each other as shown in FIG. 2. A tubular interconnecting member 73 is mounted, as by welding, so as to interconnect the distal end portions of the convergent member 72 parallel to the cross member 70 and in the same plane therewith. Tubular parallel members 74 are individually mounted, as by welding, on the interconnecting member 73 extending therefrom in parallel relation to each other toward and in right angular relation to the cross member 70, as shown in FIG. 2. Each of the parallel members has a distal end portion 75.

Each of the parallel members 74 mounts a collection assembly generally indicated at 80 on the distal end portion 75 thereof. Each of the collection assemblies has a mounting bracket 81 mounted, as by welding, on the distal end portion of the parallel member as shown best in FIG. 3. A bearing assembly 82 is mounted by any suitable means on the mounting bracket 81 of each collection assembly and defines an axis of rotation 83 which is vertical and preferably right-angularly related to the plane generally defined by the main frame 60 of the sampling apparatus.

Figure 3:
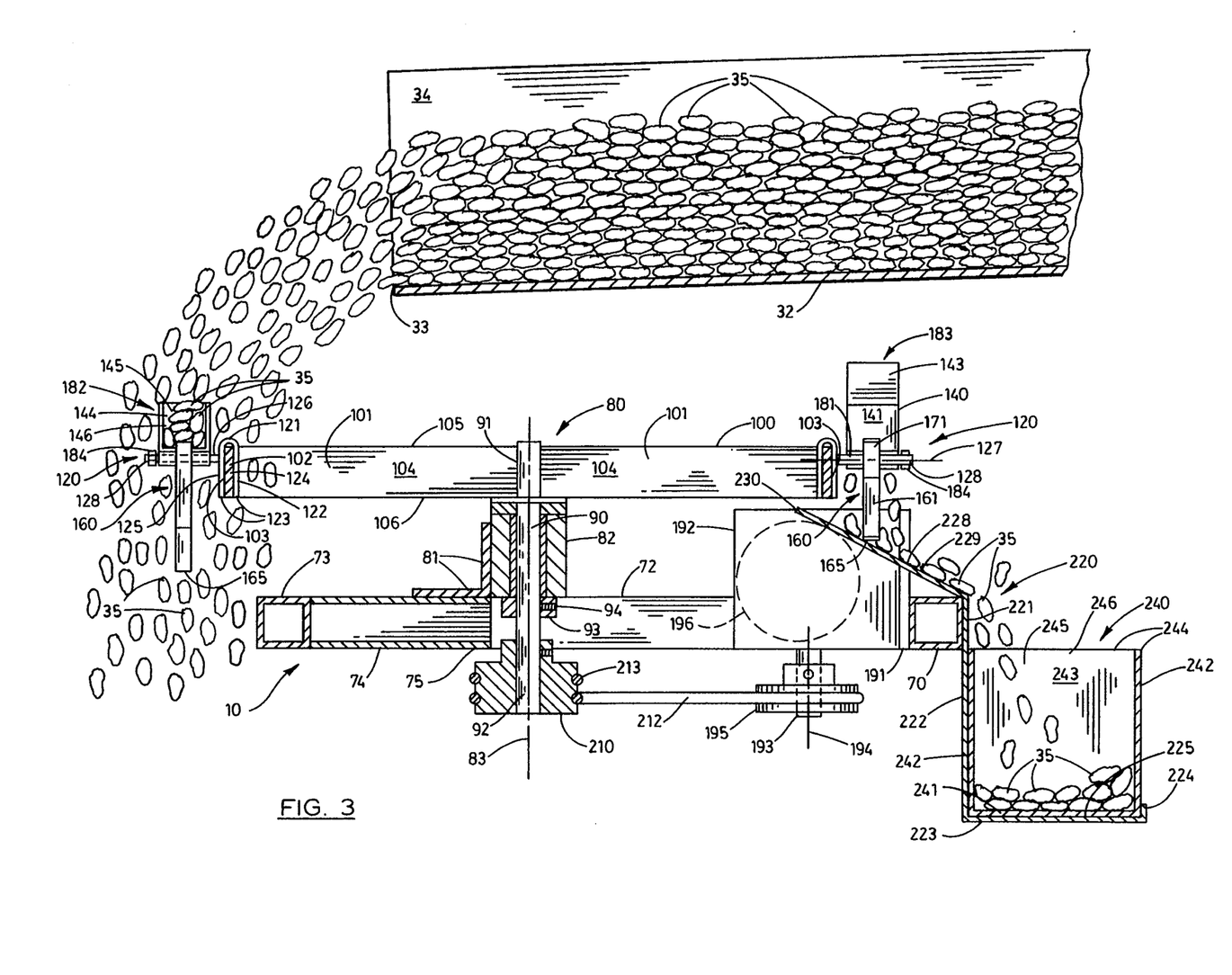
FIG. 3 is a somewhat further enlarged, fragmentary, vertical section taken on line 3—3 in FIG. 1.

A drive shaft 90 is mounted for rotational movement in each of the bearing assemblies 82 of the collection assemblies 80. Each drive shaft has an upper end portion 91 above the plane generally defined by the main frame 60 of the sampling apparatus and a lower end portion 92 below the plane generally defined by the main frame 60. A lock ring 93 is removably secured on each drive shaft to retain the drive shaft in the position described for rotation in the bearing assembly about its respective axis rotation 83. A set screw 94 extends through the lock ring and into engagement with its respective drive shaft so as to mount the drive shaft in the position described, while being removable therefrom for removal of the drive shaft from its respective bearing assembly if desired.

Each collection assembly 80 has a subframe or collection wheel 100 mounted on its respective drive shaft 90 for rotational movement therewith. Each of the collection wheels has three spoke members 101 mounted, as by welding, on the upper end portion 91 of its respective drive shaft and extending radially outwardly therefrom in substantially right angular relation to the axis of rotation 83 in equally spaced relation thereabout, as best shown in FIG. 2. A cylindrical band member 102 is mounted, as by welding, on the terminal ends of the spoke members concentric to the axis of rotation 83 thereof. The cylindrical band member has a cylindrical outer surface 103 and a cylindrical inner surface 104. The band member has an upper edge 105 and an opposite lower edge 106 parallel to the upper edge. The upper and lower edges are concentric to the axis of rotation 83 of the drive shaft 90.

Each of the collection wheels 100 mounts at least one receiving housing or collection cup assembly 120, as will hereinafter be described in greater detail. In the preferred embodiment, two such collection cup assemblies 120 are individually mounted on each collection wheel. However, it will be understood that any desired number of collection cup assemblies can be mounted on each collection wheel for use in the manner and for the purposes hereinafter to be described. Each collection cup assembly has a mounting clip 121 formed from a return bent member 122 having terminal ends 123 disposed in side-by-side relation. The return bent member thus defines a passage or slot 124 having a transverse dimension adapted to be slip fit on the band member 102 of its respective collection wheel with the band member received within the slot. The width of the slot is such that the mounting clip firmly retains its respective collection cup assembly in the position to be described while permitting it to be slidably removed therefrom when desired. The mounting clip has an outer surface 125 on which is mounted an axile or rod 126 by any suitable means such as welding. The rod is cylindrical and defines an axis of rotation 127 right-angularly related to the outer surface 125 of the mounting clip. The rod has an externally screw threaded end portion 128.

Each collection cup assembly 120 has a collection cup 140. The collection cup has a flat bottom panel 141, parallel side panels 142 fight-angularly related to and extending from the bottom panel 141 and a back panel 143 right-angularly related to the parallel side panels and to the bottom panel. The collection cup is preferably, although not necessarily, constructed of metal and defines a receptacle 144 of predetermined volume. The upper edges of the side panels 142 and the back panel 143 define a receiving opening 145 communicating with the receptacle. The front edges of the side panels 142 and of the bottom panel 141 define a discharge opening 146 communicating with the receptacle.

Figure 4:
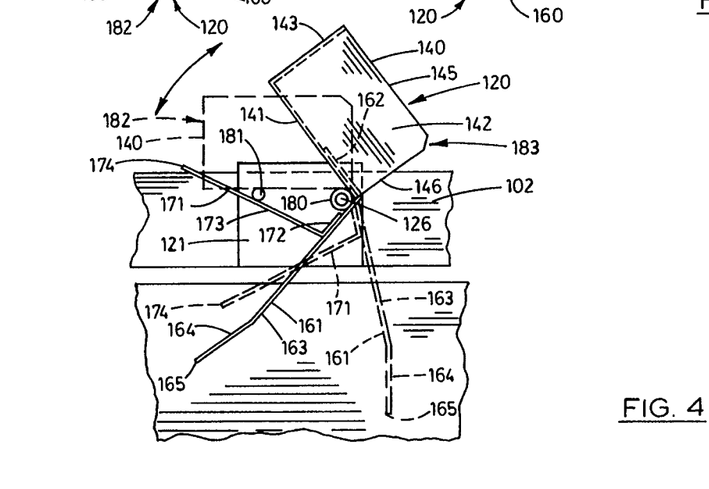
FIG. 4 is a somewhat enlarged, fragmentary, vertical section taken from a position indicated by line 4—4 in FIG. 2 and showing a collection cup assembly of the sampling apparatus of the present invention in full lines in a discharge position and in phantom lines in a receiving position.

Each of the collection cups 140 mounts a control arm, or finger assembly, 160. The control finger assembly includes a primary control arm, or finger, 161, preferably constructed of rigid, resilient metal such as spring steel, and having a mounting end portion 162 mounted, as by welding, on the interior surface of the bottom panel 141 of the collection cup. The primary control finger has a trip portion 163 extending downwardly from the bottom panel 141 of the collection cup, as best shown in FIG. 4. The trip portion of the primary control finger extends to a distal end portion 164 having a terminal edge 165. As can be seen in FIG. 4, the distal end portion 164 is slightly bent relative to the remainder of the trip portion of the primary control finger.

A secondary control arm, or finger, 171 is mounted, as by welding, on the back surface of the primary control finger 161 in adjacent spaced relation to the bottom panel 141 of the collection cup. The secondary control finger is also preferably constructed of a rigid, resilient metal such as spring steel. The secondary control finger has a mounting end portion 172 which is weldably secured on the primary control finger as described and a contact portion 173 which extends at an angle to the primary control finger as shown in FIG. 4. The contact portion 173 extends to a terminal edge 174.

A mounting sleeve 180 is mounted, by welding, on the underside of the bottom panel 141 of the collection cup and in engagement with the primary control finger 161, as shown in FIG. 4. The mounting sleeve is slidably received on the rod 126 of its respective collection cup assembly 120 for pivotal movement about the axis of rotation 127. A stop pin 181 is mounted on the outer surface 125 of the mounting clip 121 thereof in spaced, parallel relation to the rod 126 in the position shown in FIG. 4. The collection cup 140 is pivotal about the axis of rotation 127 between a receiving position 182 shown in phantom lines in FIG. 4 and a discharge position 183 shown in full lines in FIG. 4. In the receiving position, the bottom panel 141 is rested on the stop pin 181 to retain the collection cup with the receiving opening 145 disposed in upwardly facing relation and the discharge opening 146 disposed in forwardly facing relation. When the collection cup is in the discharge position, the contact portion 173 of the secondary control finger 171 engages the stop pin 181 so as to prevent the collection cup rotating farther in a clockwise direction, as viewed in FIG. 4. This ensures that the collection cup is rotated back to the receiving position 182 by gravity once released, as will hereinafter be described in greater detail. In the discharge position 183, the bottom panel 141 is disposed at the sloped angle shown in FIG. 4 with the discharge opening 146 facing in a downward direction. A nut 184 is screw-threadably secured on the externally screw threaded end portion 128 of the rod 126 to capture the mounting sleeve 180 and thereby the collection cup for pivotal movement between the receiving position and the discharge position, as heretofore described.

The sampling apparatus 10 has a drive assembly 190 having a motor and transmission mount 191 mounted by any suitable means on the cross member 170 in the position shown in FIG. 2. A transmission 192 of any suitable type is secured on the motor and transmission mount 191 between the cross member 70 and the convergent member 72 on the left, as viewed in FIG. 2. The transmission mounts a drive shaft 193 extending downwardly therefrom, as best shown in FIG. 3, for rotational movement about an axis of rotation 194 parallel to the axis of rotation 83 of the bearing assembly 82. A drive pulley assembly 195 is mounted on the drive shaft for rotation therewith about the axis of rotation 194. A suitable electric drive motor 196 is mounted on the transmission 192 in driving relation thereto and connected to a suitable source of electrical energy for operation thereof and, thus, rotation of the drive shaft in a counterclockwise direction as viewed in FIG. 2 about the axis of rotation 194.

The drive assembly 190 has a first driven pulley 210, shown in FIG. 3, mounted on the lower end portion 92 of the drive shaft 90 on the left as viewed in FIG. 2. A second driven pulley 211 is mounted on the lower end portion 92 of the drive shaft 90 on the right, as viewed in FIG. 2, for rotation about the axis of rotation 83 of its respective bearing assembly 82. A drive cable 212 is entrained about the drive pulley 195 and the first driven pulley 210 in driving relation thereto so as to rotate the drive shaft 90 and collection wheel 100 on the left, as viewed in FIG. 2, in a counterclockwise direction. A driven cable 213 is entrained about and interconnects the first driven pulley 210 and the second driven pulley 211 to transfer rotational energy therebetween. Thus, operation of the drive assembly 190 causes the drive shafts 90 and collection wheels 100 to be rotated at substantially the same number of revolutions per minute and counterclockwise directions as viewed in FIG. 2 about their respective axes of rotation 83.

A collection assembly 220 is mounted on the cross member 70 in juxtaposition to the collection wheels 100 as shown in FIG. 2 and immediately therebeneath as shown in FIG. 3. The collection assembly has a main frame 221 preferably constructed of a single sheet of metal configured so as to form the portions thereof to be described. The main frame includes a central mounting panel 222 secured, as by welding, on the cross member 70 in facing engagement therewith and extending downwardly therefrom as shown in FIG. 3. The central mounting panel has a bottom panel 223 mounted at the lower edge thereof and extending in right angular relation therefrom to the right as viewed in FIG. 3. The bottom panel terminates in a lip 224 extending upwardly therefrom a short distance parallel to the central mounting panel 222 and in predetermined spaced relation thereto. The lip, bottom panel and central mounting panel thus define a receiving channel 225. As viewed in FIG. 2, the receiving channel has a left edge 226 and an opposite right edge 227. The main frame further includes an upper receiving panel 228 extending obliquely upwardly and to the left, as viewed in FIG. 3, from the cross member 70 and having a flat upper surface 229. The upper receiving panel terminates in an upper edge 230 beneath the collection wheels 100. The upper receiving panel has a left lateral edge 231 and a fight lateral edge 232, as shown in FIG. 2. The corner of the upper receiving panel on the fight, as viewed in FIG. 2, is bent downwardly at an angle to form a ridge 234 oblique to the upper edge 230 of the upper receiving panel and transversely related to the band member 102 of the collection wheel thereabove.

A trough, or receiving container, 240 is slidably received in the receiving channel 225 of the collection assembly 220. The receiving container has a flat bottom wall 241 and upstanding, parallel side walls 242 fight-angularly related to the bottom wall and disposed in predetermined spaced relation. A pair of end walls 243 are mounted on and interconnect the bottom wall and side walls at opposite ends of the receiving container. The side walls and end walls have upper edges 244 forming a rectangle. The receiving container has an internal receptacle 245, a predetermined volume, and defined by the bottom wall, side walls and end walls. The upper edges 244 define a mouth 246 communicating with the receptacle. As can best be visualized in FIG. 3, the receiving container is slidably received in the receiving channel 225 for movement from the receiving channel to the fight or left as viewed in FIG. 2.

OPERATION

The operation of the described embodiment of the present invention is believed to be readily apparent and is briefly summarized at this point. In the illustrative embodiment, the sampling apparatus 10 is mounted on the raisin shaker table 20 beneath the discharge chute 31 in the relationship shown in FIG. 3. Such installation is accomplished simply by individually sliding the tubular sleeves 61 of the main frame 60 onto the mounting rods 50, sliding the main frame to the desired position, and tightening the bolts 64 into engagement with the mounting rods releasably to lock the main frame in the desired position, such as shown in FIG. 2.

In the illustrative embodiment herein described, two collection cup assemblies 120 are mounted on each collection wheel 100 and positioned one hundred and eighty degrees (180°) from each other, as shown in FIG. 2. As previously noted, any desired number of collection cup assemblies can be so mounted on each collection wheel about the cylindrical band member 102 thereof in accordance with the quantity of the sample desired for a given period of operation.

When operation of the sampling apparatus 10 is desired, the electric drive motor 196 is connected to a source of electrical energy, not shown, to supply electrical energy to the drive motor and thereby operate the sampling apparatus. If desired, any suitable electrical circuit can be employed including an on/off switch and an individual source of electrical energy permitting activation of the sampling apparatus to be initiated simply by closing the switch.

Upon activation of the sampling apparatus 10, the collection assemblies 80 are activated to rotate the collection wheels 100 at substantially the same number of revolutions per minute in counterclockwise directions as viewed in FIG. 2. During rotation of the collection wheels, throughout most of the three hundred and sixty degrees (360°) of movement about the axes of rotation 83, the collection cup assemblies are disposed in their receiving positions 182 as shown on the left in FIG. 3. As each collection cup assembly of the collection wheel on the left as viewed in FIG. 2 approaches the upper edge 230 of the upper receiving panel 228, its respective primary control finger 161, or more precisely the trip portion 163 thereof, is drawn into engagement with the upper edge 230. In the case of the collection wheel on the fight as viewed in FIG. 2, the primary control finger 161 of each collection cup assembly is drawn into engagement with the ridge 234. As each collection wheel continues to rotate in the counterclockwise direction, the primary control finger 161 is drawn over the upper edge 230, or ridge 234, so as to cause the collection cup assembly to be pivoted in a clockwise direction, as viewed in FIG. 4, from the receiving position 182 to the discharge position 183. As such movement is continued, the terminal edge 165 of the primary control finger rides along the upper surface 229 of the upper receiving panel as may best be visualized in FIG. 3. This retains the collection cup assembly in the discharging position shown in FIG. 4 for as long as the collection cup is over the upper surface 229 of the upper receiving panel 228. The secondary control finger 171 operates to prevent the collection cup assembly from being pivoted farther than the discharge position in the clockwise direction, as viewed in FIG. 4, during such passage over the upper receiving panel 228. Accordingly, when the primary control finger passes over the edge of the upper receiving panel and from engagement therewith, the receiving cup assembly is returned gravitationally to the receiving position 182 shown in FIG. 4 in phantom lines. This same process is repeated for both receiving cup assemblies of both collection wheels.

With the sampling apparatus 10 operating in the manner described, the raisin shaker table 20 is operated in the conventional manner. Thus, a bin of raisins to be processed is dumped into the hopper 25 after the control housing 26 has been activated to reciprocate the screen assembly 24 in the manner previously described. Thus, a layer of raisins to be processed is distributed substantially evenly on the screen assembly by the hopper, transported over the screen assembly and reciprocated to release foreign matter, such as trash, therefrom. The raisins pass into the discharge chute 31 moving from right to left, as viewed in FIG. 3. The mass of raisins then flows in a substantially continuous stream over the lip 33 of the discharge chute along the path shown in FIG. 3 and thus continuing in a substantially continuous stream.

With the sampling apparatus 10 operating in the manner described, each successive collection cup 140 is passed into and through the substantially continuous stream of raisins thus filling the receptacle 144 of the collection cup with raisins now constituting part of the collected sample. The raisins are transported in their respective collection cups along the path previously described until the collection cups reach the positions described over the upper receiving panel 228. The predefined movement of each successive collection cup to its respective discharge position 183 causes the raisins contained therewithin to fall gravitationally from their respective collection cups onto the upper surface 229 of the upper receiving panel 228. The raisins are moved gravitationally along the upper surface, over the cross member 70 and into the receptacle 245 of the receiving container 240, as shown in FIG. 3.

The foregoing operation continues automatically during operation of the raisin shaker table 20 thereby filling the receiving container 240 with the raisins constituting the sample from the raisins contained in the bin dumped in the receiving hopper 25. If the receiving container fills with raisins, personnel can remove the receiving container, empty its contents into another container and return the receiving container to the position shown in FIG. 3 for continued collection of the raisins constituting the sample. However, the volume of the receiving container is such that this need not be done until another raisin bin is emptied into the receiving hopper 25. The raisins thus collected as part of the sample are then tested and otherwise examined in accordance with conventional inspection processes for purposes, for example, of establishing a grade for the raisins contained in the bin from which the raisins were collected is the sample.

Adjustment of the quantity of raisins collected to form the sample may be achieved by increasing or decreasing the number of revolutions per minute of rotation of the collection wheels 100 and/or increasing the number or reducing the number of collection cup assemblies borne by the collection wheels.

Therefore, the sampling apparatus of the present invention is adaptable for use in sampling a wide variety of types of material in a wide variety of environments; is particularly well suited to the sampling of fungible goods transported in a substantially continuous steam; is significantly more reliable than conventional methods and apparatuses intended for the same purpose; is uniquely effective in the sampling of lots of raisins during processing; operates substantially automatically with little or no attention by personnel; is entirely safe and dependable in operation and is inexpensive to install, maintain and operate; and is otherwise entirely successful in achieving its operational objectives.

Although the invention has been herein shown and described in what is conceived to be the most practical and preferred embodiment, it is recognized that departures may be made therefrom within the scope of the invention which is not to be limited to the illustrative details disclosed.

Having described our invention, what we claim as new and desire to secure by Letters Patent is:

1. An apparatus for collecting material from a mass of said material released from a source thereof, the apparatus comprising means for collecting the material; a container for holding the material; an assembly mounted on said source and mounting the collecting means for movement along a path through said mass of material, for the collection of a portion of the material by the collecting means, and toward the container, for the release of said material thereinto and for movement between a receiving position, oriented to receive said material, and a discharging position, oriented to discharge said material therefrom; and first and second surfaces borne by the collecting means for controlling movement of said collection means between said receiving position and said discharging position during movement in said path.

2. The apparatus of claim 1 wherein said first and second surfaces are deployed for individual engagement by predetermined contact surfaces one of which is adjacent to said container for moving the collecting means to the discharging position and the other of which is adjacent to the collecting means for limiting movement of the collecting means beyond said discharging position.

3. The apparatus of claim 2 wherein said collecting means is mounted on the assembly for substantially pivotal movement between the receiving position and the discharging position and wherein said predetermined contact surface for the second surface is a member which supports the collecting means in rested relation thereon in the receiving position and which is engageable by the second surface to prevent pivoting of the collecting means beyond the discharging position.

4. The apparatus of claim 3 wherein said first and second surfaces are borne by first and second arms respectively mounted on and extending substantially downwardly from the collecting means for engagement with said predetermined contact surfaces in moving the collecting means between said receiving and discharging positions.

5. The apparatus of claim 1 wherein said collecting means is a housing, having a receptacle for receiving said material, the housing is mounted for substantially pivotal movement about a pivot pin, a member is disposed in spaced relation to said pivot pin and the housing is limited in movement between said receiving and discharging positions by individual engagement by said member with the housing and alternatively said second surface in said substantially pivotal movement about the pivot pin.

6. An apparatus for sampling material from a substantially continuous stream of said material released from a source thereof along a predetermined path, the apparatus comprising:
- A. a main frame adapted to be mounted on said source in an operational position adjacent to said predetermined path;
- B. a subframe mounted on the main frame for rotational movement about an axis of rotation adjacent to said predetermined path;
- C. a receiving housing, having a receptacle dimensioned for the receipt of said material, mounted on the subframe for substantially pivotal movement about an axis of rotation transversely related to the axis of rotation of the subframe between a receiving attitude, in which the receptacle thereof is disposed in substantially upwardly facing relation, and a discharging attitude, in which said receptacle is disposed for the gravitational release of material therefrom;
- D. a collection assembly mounted on the main frame in a collection station disposed in spaced relation to said predetermined path including a collection container, having a mouth communicating with a receptacle for said material, mounted in a receiving position with said mouth disposed in a generally upwardly facing attitude;
- E. means for rotating the subframe about said axis of rotation to transport the receiving housing through said predetermined path and said collection station in successive cycles of rotation about said axis of rotation;
- F. means for retaining the receiving housing in said receiving attitude during passage through said predetermined path and for moving the receiving housing to the discharging attitude during passage through the collection station, whereby, during release of said substantially continuous stream of said material from the source in each successive cycle of rotation, a portion of the material is received in the receiving housing and discharged into the collection container so as to create a sample of said material; and
- G. wherein said retaining and moving means includes a pair of arms, consisting of a first arm and a second arm, mounted on the receiving housing and extending downwardly therefrom, a support disposed in spaced relation to said axis of rotation of the receiving housing in supporting relation to the receiving housing when the receiving housing is in the receiving attitude and engageable by the first arm of said pair of arms to prevent the receiving housing rotating beyond the discharging attitude, the receiving housing is balanced so as gravitationally to be retained in the receiving attitude and means for engaging the second arm of said pair of arms in the collection station to pivot the receiving housing from the receiving attitude to the discharging attitude to discharge said portion of the material therefrom and thereafter to release said second arm of said pair of arms for gravitational return of the receiving housing to the receiving attitude.

7. The apparatus of claim 6 including a panel mounted in the collection station sloping toward the collection container in material feeding relation thereto and wherein said engaging means is a portion of said panel.

* * * * *

UNITED STATES PATENT AND TRADEMARK OFFICE
CERTIFICATE OF CORRECTION

PATENT NO. : 5,398,558

DATED : March 21, 1995

INVENTOR(S) : Jack C. Wise; Carter D. Clary; Gwynn A. Sawyer Ostrom

It is certified that error appears in the above-identified patent and that said Letters Patent is hereby corrected as shown below:

Column 1, line 57, delete "frown" and substitute "from".

Column 7, line 54, delete "fight" and substitute "right".

Column 8, line 48, delete "fight" and substitute "right".

Signed and Sealed this

Sixteenth Day of May, 1995

*Attest:*

BRUCE LEHMAN

*Attesting Officer*      *Commissioner of Patents and Trademarks*